(12) United States Patent
Heringslack

(10) Patent No.: US 8,189,801 B2
(45) Date of Patent: May 29, 2012

(54) EAR CUP

(75) Inventor: Henrik Heringslack, Varnamo (SE)

(73) Assignee: 3M Svenska Aktiebolag, Sollentuna (SE)

( * ) Notice: Subject to any disclaimer, the term of this patent is extended or adjusted under 35 U.S.C. 154(b) by 1242 days.

(21) Appl. No.: 11/912,434

(22) PCT Filed: Apr. 26, 2006

(86) PCT No.: PCT/SE2006/000497
§ 371 (c)(1),
(2), (4) Date: Oct. 24, 2007

(87) PCT Pub. No.: WO2006/118515
PCT Pub. Date: Nov. 9, 2006

(65) Prior Publication Data
US 2008/0192973 A1    Aug. 14, 2008

(30) Foreign Application Priority Data
Apr. 29, 2005   (SE) ..................................... 0500982

(51) Int. Cl.
    G10K 11/16   (2006.01)
    H03B 29/00   (2006.01)
(52) U.S. Cl. ................... 381/71.6; 381/71.7; 381/72
(58) Field of Classification Search ............ 381/71.6, 381/71.7, 72
    See application file for complete search history.

(56) References Cited

U.S. PATENT DOCUMENTS

| | | | |
|---|---|---|---|
| 2,235,372 A * | 3/1941 | Kalbitz ..................... | 381/371 |
| 3,087,028 A | 4/1963 | Bonnin | |
| 3,306,991 A | 2/1967 | Wood | |
| 3,394,226 A | 7/1968 | Andrews, Jr. | |
| 3,456,263 A * | 7/1969 | Aileo ..................... | 2/423 |
| 3,579,640 A * | 5/1971 | Begiun et al. ..................... | 2/209 |
| 3,833,939 A * | 9/1974 | Dostourian ..................... | 2/209 |
| 3,869,584 A | 3/1975 | Wilde | |

(Continued)

FOREIGN PATENT DOCUMENTS

DE   10117704   6/2001

(Continued)

OTHER PUBLICATIONS

International Search Report; PCT/SE2006/000497; Aug. 8, 2006.

*Primary Examiner* — David S. Warren

(57) ABSTRACT

An ear cup which comprises an inner cup portion for the formation of a noise damping space and an outer cup portion for the formation of a space for accommodating electronics, electrical connections and/or a current source. The outer cup portion is fixable on the inner with the aid of a locking member which is insertable in a guide in the outer cup portion. The inner cup portion has a locking recess and the outer cup portion has an aperture. The locking member is placed in the locking recess and the aperture. The locking member has an outer shank and an inner shank. The outer shank is provided with a bulge which engages with a recess in the outer cup portion. The inner shank is provided with a locking portion which engages with the inner cup portion. The locking portion has projections which prevent withdrawal of the inner shank out of the aperture. In association with the projections, recesses are provided which, together with recesses in the outer cup portion, entail that the locking member can "be wriggled" into position in the aperture. The ear cup is designed in order to realise simple and rational assembly of the components included.

11 Claims, 6 Drawing Sheets

U.S. PATENT DOCUMENTS

| | | | |
|---|---|---|---|
| 3,890,474 A | 6/1975 | Glicksberg | |
| 3,952,158 A | 4/1976 | Kyle | |
| 4,027,113 A * | 5/1977 | Matsumoto et al. | 381/378 |
| 4,064,362 A | 12/1977 | Williams | |
| 4,066,849 A * | 1/1978 | Chladil, Sr. | 381/371 |
| 4,087,653 A | 5/1978 | Frieder, Jr. | |
| 4,302,635 A * | 11/1981 | Jacobsen et al. | 381/371 |
| 4,327,257 A * | 4/1982 | Schwartz | 381/405 |
| 4,677,678 A | 6/1987 | McCutchen | |
| 4,829,571 A | 5/1989 | Kakiuchi | |
| 4,833,719 A | 5/1989 | Carme | |
| 4,867,149 A | 9/1989 | Falco | |
| 4,928,311 A | 5/1990 | Trompler | |
| 4,965,836 A * | 10/1990 | Andre et al. | 381/370 |
| 4,985,925 A | 1/1991 | Langberg | |
| 5,125,032 A | 6/1992 | Meister | |
| 5,181,252 A | 1/1993 | Sapiejewski | |
| 5,251,263 A | 10/1993 | Andrea | |
| 5,402,497 A * | 3/1995 | Nishimoto et al. | 381/95 |
| 5,497,427 A | 3/1996 | Nageno | |
| 5,519,783 A * | 5/1996 | Kumar | 381/370 |
| 5,550,923 A | 8/1996 | Hotvet | |
| 5,631,965 A | 5/1997 | Chang | |
| 5,675,658 A | 10/1997 | Brittain | |
| 6,631,279 B2 | 10/2003 | Rivera | |
| 6,704,428 B1 | 3/2004 | Wurtz | |
| 6,724,906 B2 * | 4/2004 | Naksen et al. | 381/379 |
| 6,728,388 B1 * | 4/2004 | Nageno et al. | 381/381 |
| 6,748,087 B1 | 6/2004 | Jones | |
| 6,801,629 B2 | 10/2004 | Brimhall | |
| 6,965,681 B2 | 11/2005 | Almqvist | |
| 6,970,571 B2 | 11/2005 | Knorr | |
| 7,099,485 B2 | 8/2006 | Dittli | |
| 7,245,735 B2 | 7/2007 | Han | |
| 7,308,106 B2 | 12/2007 | Vaudrey | |
| 7,327,850 B2 | 2/2008 | Crump | |
| 7,391,878 B2 * | 6/2008 | Liao | 381/370 |
| 7,664,282 B2 | 2/2010 | Urso | |
| 2001/0046304 A1 | 11/2001 | Rast | |
| 2002/0001391 A1 * | 1/2002 | Darbut | 381/122 |
| 2002/0003889 A1 * | 1/2002 | Fischer | 381/370 |
| 2004/0125976 A1 * | 7/2004 | Reneker | 381/372 |
| 2004/0125977 A1 * | 7/2004 | Hong et al. | 381/376 |
| 2005/0201580 A1 * | 9/2005 | Dittli | 381/322 |
| 2007/0183606 A1 | 8/2007 | Doty | |
| 2007/0274529 A1 * | 11/2007 | Nordin et al. | 381/72 |
| 2008/0011084 A1 | 1/2008 | Von Dach | |
| 2008/0192973 A1 * | 8/2008 | Heringslack | 381/372 |
| 2008/0279411 A1 * | 11/2008 | Suzuki et al. | 381/386 |
| 2011/0124300 A1 * | 5/2011 | Sinai | 455/74 |

FOREIGN PATENT DOCUMENTS

| | | |
|---|---|---|
| EP | 0465971 A2 | 1/1992 |
| EP | 0967592 | 12/1999 |
| EP | 1629808 A1 | 3/2006 |
| FR | 2695302 | 3/1994 |
| GB | 1160431 A | 8/1969 |
| GB | 1289993 A | 9/1972 |
| GB | 2445984 A | 7/2008 |
| WO | WO 87/04065 | 7/1987 |
| WO | WO 91/07153 | 5/1991 |
| WO | WO 96/08004 | 3/1996 |
| WO | WO 97/28742 A1 | 8/1997 |
| WO | WO 02/17838 | 3/2002 |
| WO | 03086124 | 10/2003 |
| WO | WO 2005/051255 | 6/2005 |
| WO | WO 2006/118514 | 11/2006 |
| WO | WO 2008/099137 | 8/2008 |
| WO | WO 2008/113822 | 9/2008 |

* cited by examiner

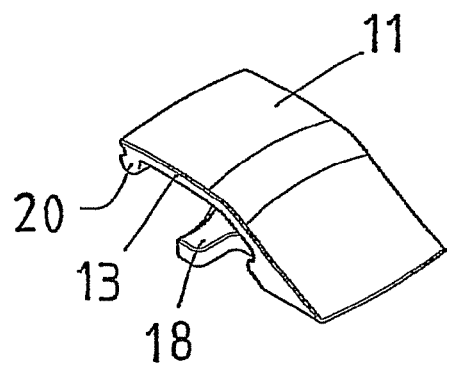
Fig 6
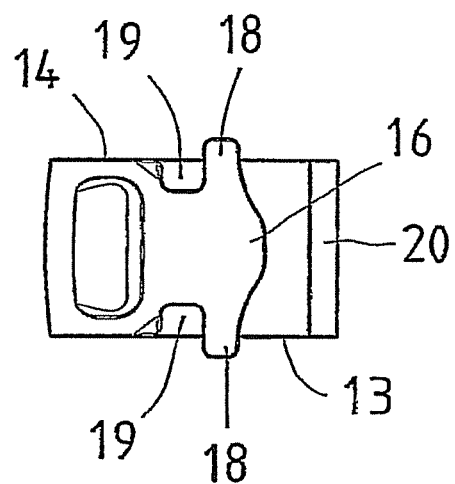
Fig 7
Fig 8
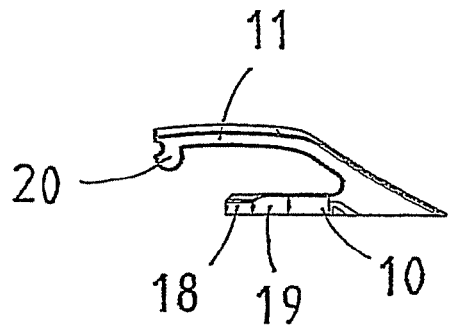

EAR CUP

TECHNICAL FIELD OF THE INVENTION

The present invention relates to an ear cup which includes an inner cup portion for forming a noise damping space and an outer cup portion for forming a space for accommodating electronics, electric connections and/or a current source, the outer cup portion being fixable on the inner.

BRIEF DESCRIPTION OF RELATED ART

Ear cups of the type described by way of introduction are previously known in the art and in numerous different designs. In one example of a prior art hearing protection apparatus, the inner cup portion has, on its outside, an opening in which a small hatch or lid is insertable. On the inside of this lid, there is then disposed a circuit card with electronics, but also the loudspeaker which is intended to provide sound reproduction inside the hearing protection. The lid with the components mounted thereon is fixedly screwed in position in the inner cup portion. For access to the battery that drives the electronics in the prior art hearing protection cup, the lid has an opening on its outside for insertion and removal of batteries, and this opening may be closed by means of a separate, smaller hatch or lid secured in place by snap anchorage.

The mounting of the electronics and the loudspeaker as a unit on the inside of the lid certainly makes mounting of the electronics simple. However, this must be bought at the cost of a large opening (which is difficult to close) for the loudspeaker in an interjacent wall in the inner cup portion.

Further drawbacks with the prior art hearing protection ear cup are the risk that the small battery lid or hatch is lost.

BRIEF SUMMARY OF THE INVENTION

The invention provides and ear cup configured so that it permits mounting of electronics in a simple and rational manner, no loose parts occur and the ear cup can, in its entirety, be assembled in a rational manner.

The ear cup comprises a locking device which includes a locking member disposed in a guide in the outer cup portion, the locking member being movable between a locked position, where the outer cup portion is fixed on the inner, and an open position, where the outer cup portion is removable from the inner, and the locking member and the outer cup portion have mutually cooperating retainer means for fixedly retaining the locking member on the outer cup portion, also in the open position.

In one particular embodiment of the invention, the outer cup portion covers the whole of the outside of the inner cup portion, and that electronics and/or a current source are mounted thereon.

BRIEF DESCRIPTION OF THE DRAWINGS

The present invention will now be described in greater detail hereinbelow, with particular reference to the accompanying Drawings. In the accompanying Drawings:

FIG. 6 is a perspective view of the locking member dismounted out of the outer cup portion;

FIG. 7 shows the locking member according to FIG. 6 seen straight from the inside; and FIG. 8 shows the locking member according to FIGS. 6 and 7 seen in a straight side elevation.

DETAILED DESCRIPTION OF THE INVENTION

The ear cup according to the present invention is included in a hearing protection unit which is provided with the possibility for communication or which is equipped with broadcast radio, or both. The hearing protection comprises two ear cups and a crown stirrup strap interconnecting them. To the extent directional and positional disclosures occur in the body of the description below, these refer to a situation where the hearing protection is worn in the normal manner using the crown strap extending across the head of the wearer. This implies, for example, that the expression 'inner' relates to something that is turned to face in towards the head of the wearer, while, on the other hand, the expression 'outer' implies something that is turned to face out away from the head of the wearer.

Figure 1:
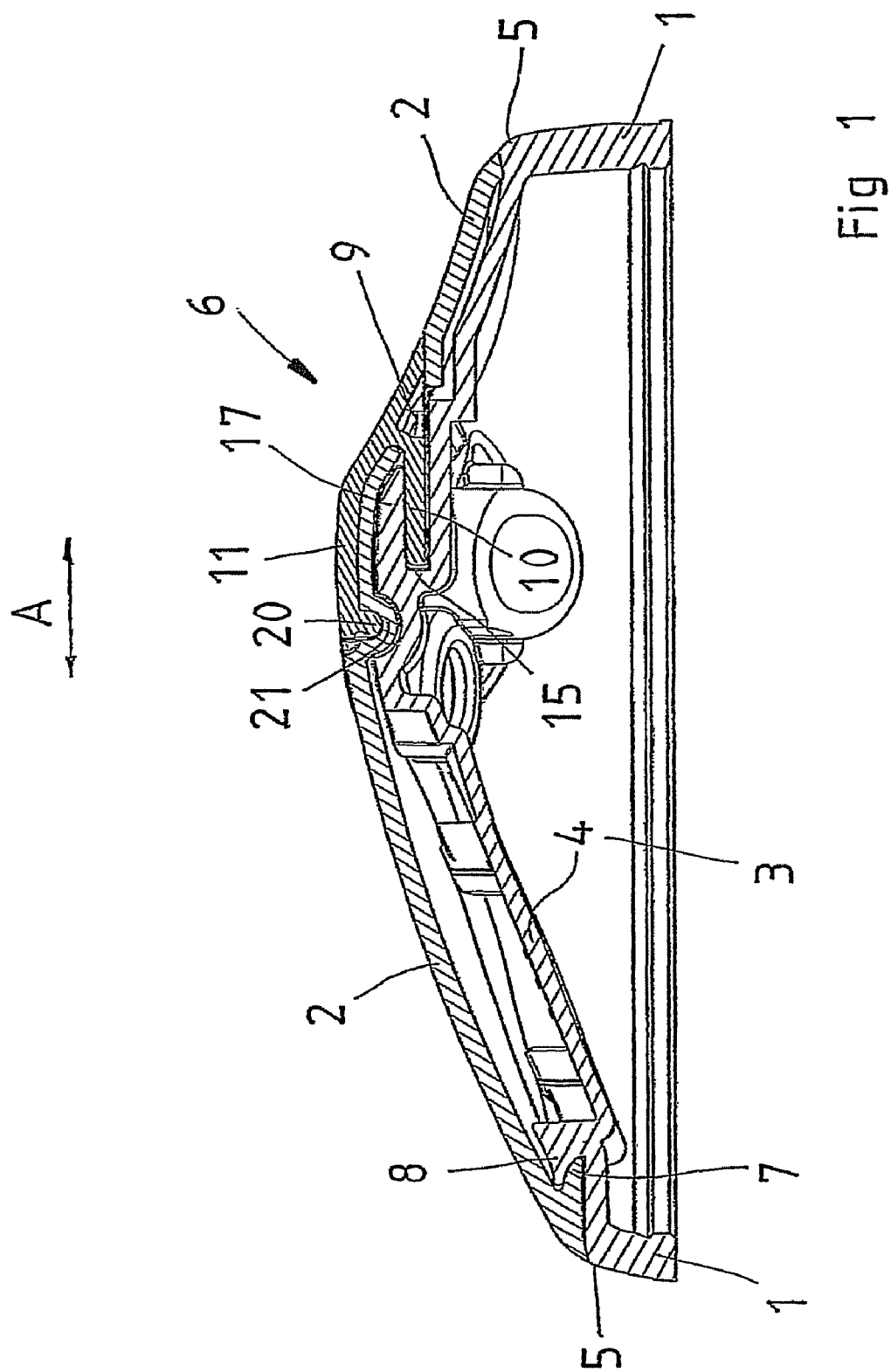
FIG. 1 is a vertical cross section through an ear cup according to the present invention.

It will be apparent from FIG. 1 that the ear cup according to the invention has an inner cup portion 1 and an outer cup portion 2. The inner cup portion 1 has for its purpose to define an enclosed, noise-damping space 3 which outwardly (upwardly in the Figure) is closed by means of a partition 4. The partition 4 has an outside which, in its entirety, is free and readily accessible and which, depending on the embodiment, is intended for mounting of electronics, microphone, loudspeaker, battery or the like. The exact design of those details which is required for such mounting of components forms no germane part of the present invention and, as a result, will not be described in greater detail below. Further, to the extent the partition 4 has any opening, this is small and easy to close and seal.

The purpose of the outer cup portion 2 is to realise a space for accommodating electronics and/or a current source or the like, in other words such components as may be mounted on the outside of the partition 4.

In order to permit simple mounting and access of the components that may be mounted on the outside of the partition 4 of the inner cup portion 1, the outer cup portion 2 is so large that it covers the whole of the outside of the inner cup portion. Otherwise expressed, the outer cup portion 2 extends all the way out to the periphery 5 of the inner cup portion, for which reason the outside of the partition 4 is completely exposed when the outer cup portion 2 is dismounted.

For mounting of the outer cup portion 2 on the inner cup portion 1, the outer cup portion 2 has a locking device by means of which the whole of the outer cup portion may be released from the inner cup portion.

Figure 5:
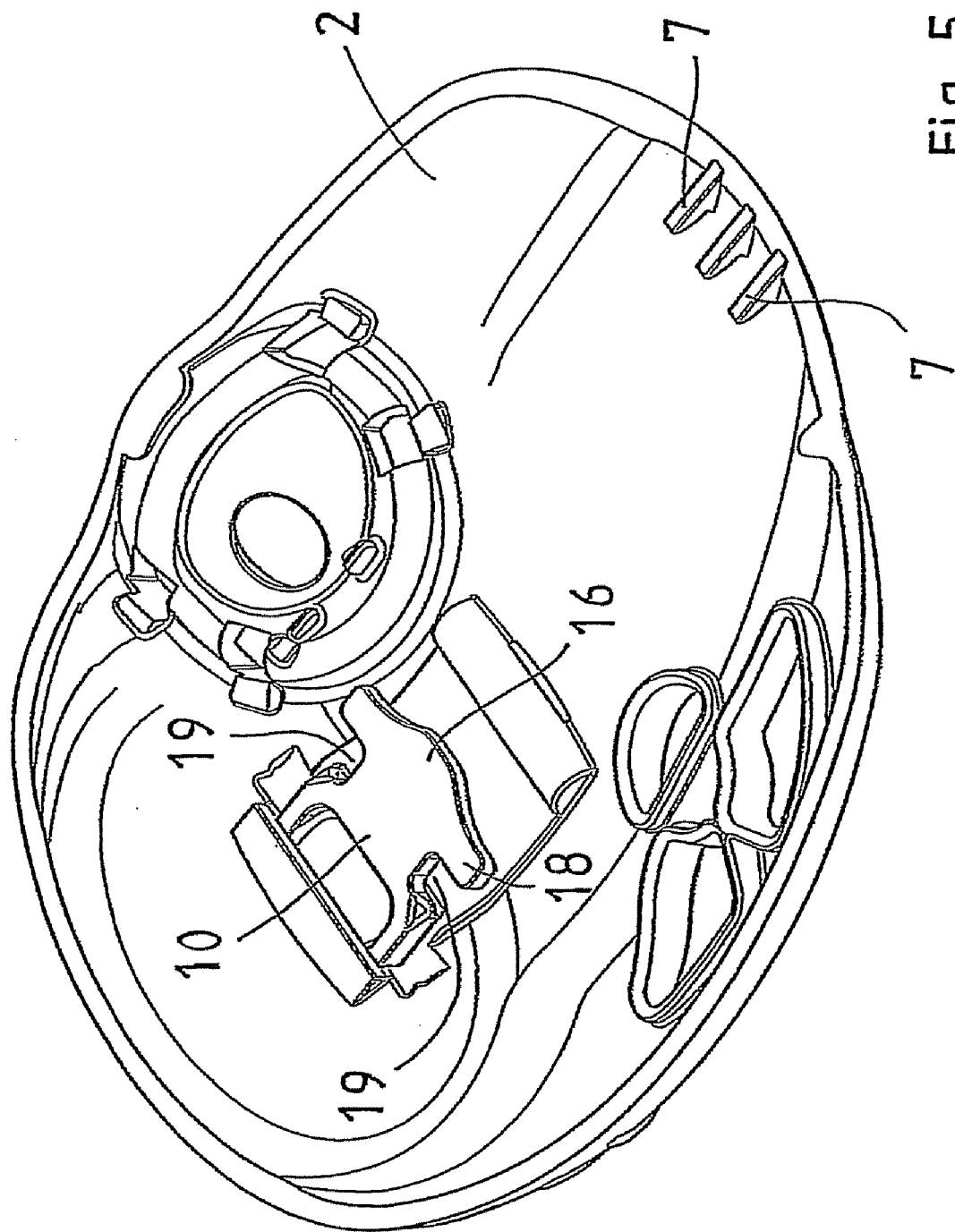
FIG. 5 is a view corresponding to that of FIGS. 3 and 4 where the locking member is located in a closed position.

It will be apparent from FIG. 1 that the locking device includes a locking member 6 which, in a guide on the outer cup portion, is movable between a locked position (according to FIG. 1) and an open position, which is not shown in FIG. 1 but rather in FIG. 5. The locking device further includes mutually engaging catch means 7 and 8 on the outer cup portion 2 and the inner cup portion 1. These catch means are shown in the left-hand part of FIG. 1.

Figure 2:
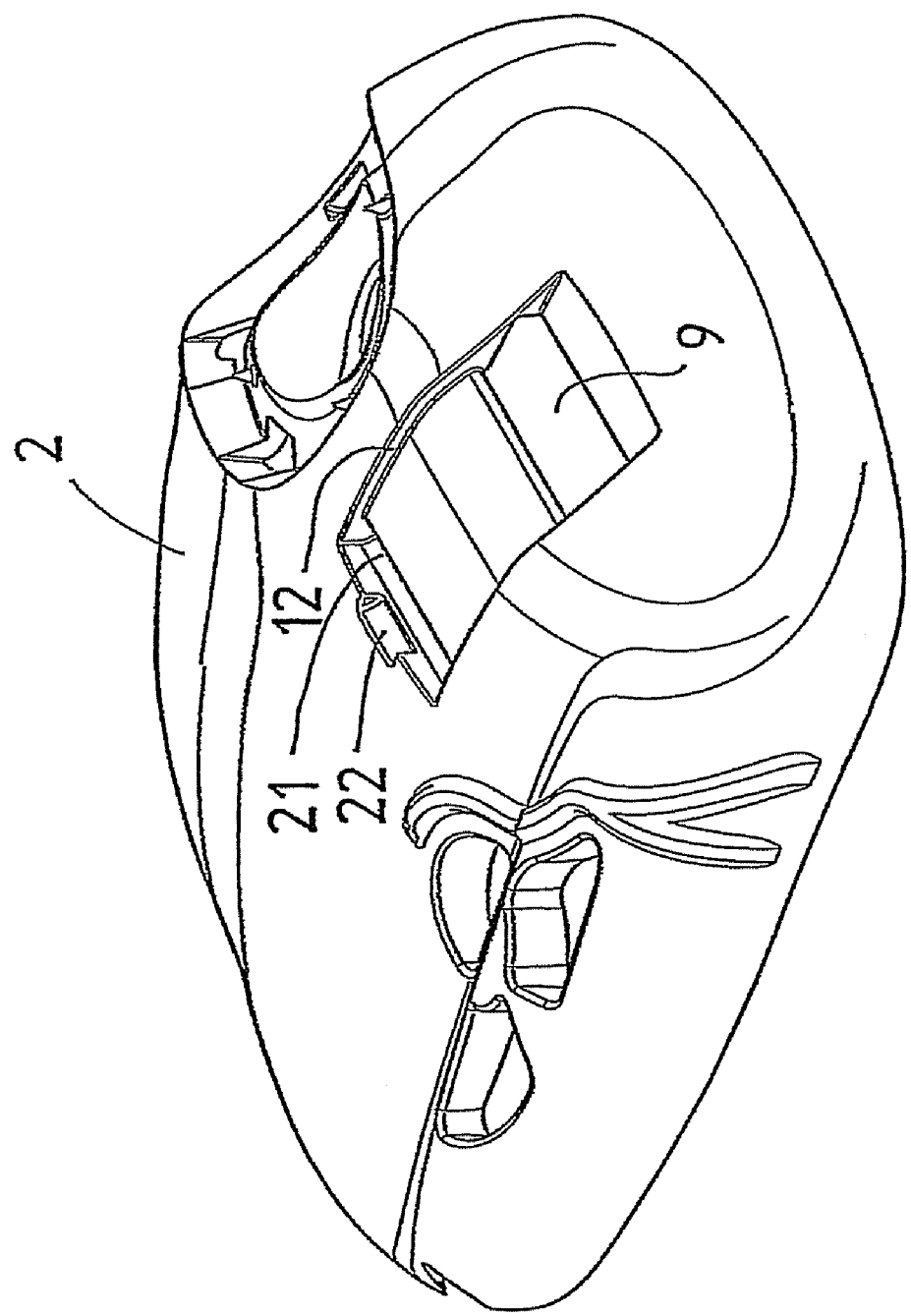
FIG. 2 is a perspective view of an outer cup portion included in the ear cup, seen from the outside.

It will be apparent from FIG. 2 that the outer cup portion 1 has an aperture 9 through which the locking member 6 is intended to extend. The locking member 6 has, as is most clearly apparent from FIGS. 1, 6 and 8, an inner shank 10 and an outer shank 11, the inner shank being intended to be located on the inside of the outer cup portion 2, while the outer shank 11 is intended to be located in a guide on the outside of the outer cup portion 2. This guide is formed by a depression defined by two opposing walls 12 in the outside of the outer cup portion 2. Both of these walls 12 are intended to abut against opposing side edges 13 and 14 on the outer shank 11 of the locking member 6. As a result, the locking member will be reciprocally slidable parallel with the double arrow A in FIG. 1.

It will also be apparent from the same Drawing figure that the inner cup portion 1 has a locking recess 15 into which the inner shank 10 is insertable with a locking portion 16.

It will be apparent from FIG. 1 that, when the inner shank 10 of the locking member 6 is slid to the locking position, the outer cup portion 2 cannot be displaced to the left in FIG. 1, since the inner shank 10 bottoms out in the locking recess 15. Nor can the outer cup portion be lifted out from the inner cup portion, since the inner shank 10 is located behind a projection 17 on the outside of the inner cup portion. Nor can the outer cup portion be displaced in a direction to the right in FIG. 1, since such a movement would be prevented by both of the catch means 7 and 8.

On opening of the locking members, the locking member 6 is displaced in a direction to the right in FIG. 1 so far that the inner shank 10 departs from the locking recess 15. This implies that, in FIG. 1, the outer cup portion 2 could be lifted upwards and then be displaced in a direction to the left, so that the catch means 7 and 8 release. The mounting of the outer cup portion 2 on the inner cup portion takes place in the reverse order.

Figure 3:
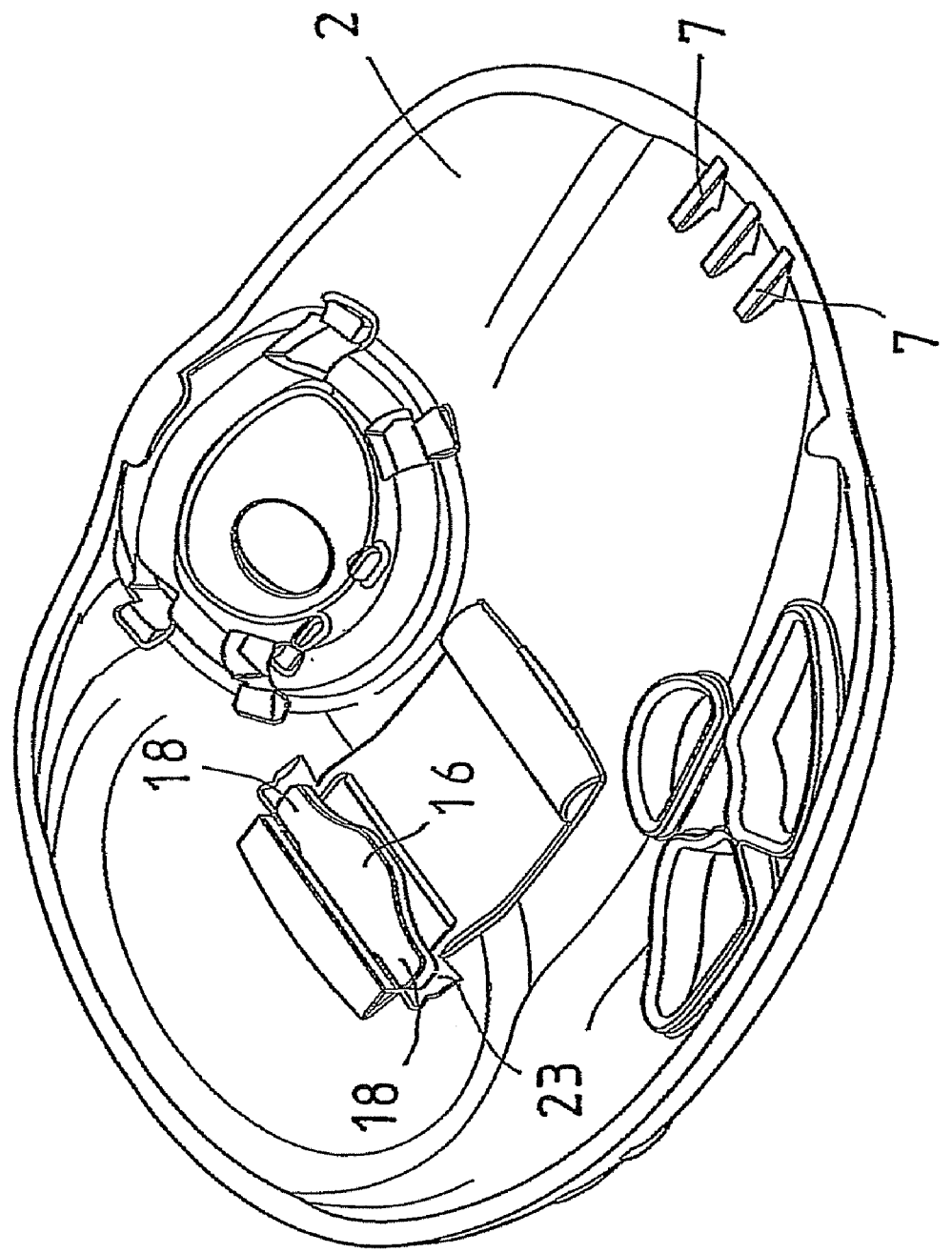
FIG. 3 shows the outer cup portion illustrated in FIG. 2, seen from the inside, with a locking member in the open position.
Figure 4:
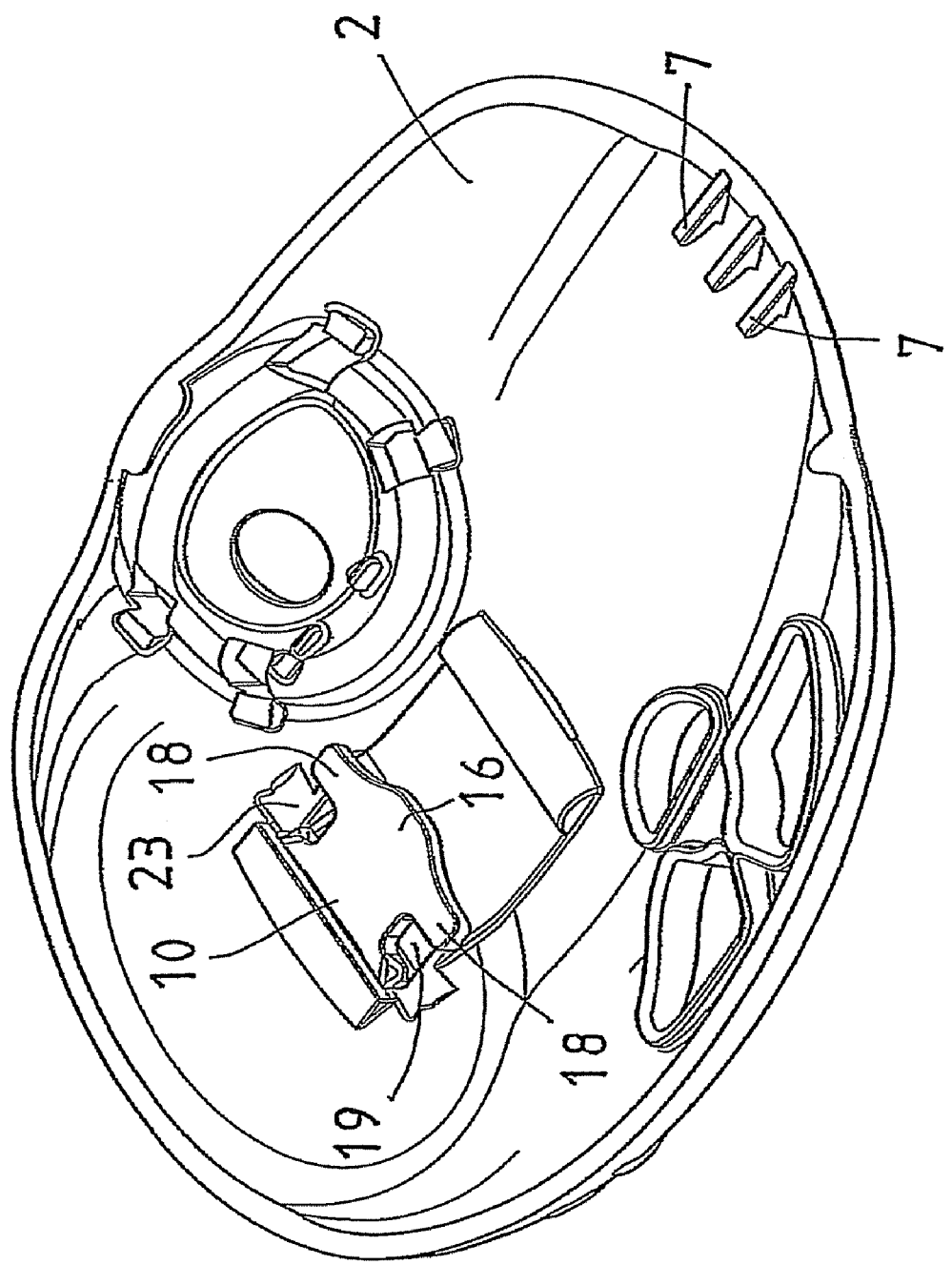
FIG. 4 is a view corresponding to that of FIG. 3 where, however, the locking member is located in an intermediate position.

FIGS. 3 to 5 show the outer cup portion from the inside, and it will be clearly apparent that the locking member in FIG. 3 is located in the open position, while in FIG. 4 it is located in an intermediate position in order, in FIG. 5, to be located in the locking position. The catch means 7 on the inside of the outer cup portion 2 are also clearly apparent.

According to the present invention, it is important that the ear cup has no loose small parts that might possibly be lost in the event of careless handling. One example of such a small part could be the locking member 6. In order to retain the locking member 6 on the outer cup portion 2, the locking member is provided with retainer means in the form of projections 18 projecting in opposing directions from the in inner shank of the locking member at its locking portion 16. These projections have such an extent beyond the width of the inner shank that this prevents withdrawal of the inner shank through the aperture 9 in the outer cup portion.

In order to make for mounting of the locking member 6 in the outer cup portion 2, the inner shank has two recesses 19 disposed in opposing edges in conjunction with the projections 18. It will be apparent from FIG. 7 that the depth of the recesses 19 in the width direction of the inner shank is larger than the extent of the projections 18 outside the opposing side edges 13 and 14 of the locking member. This implies that, by a lateral displacement of the locking member transversely of the extent of the walls 12, it is possible to cause a defining edge for the aperture 9 to be located in either of the recesses 19. Since the recess is deeper than the extent of the oppositely located projection 18, the locking member can "be wriggled into the aperture", but also be dismounted therefrom by a reverse movement pattern. In order for this to be possible, it is only necessary that the outer shank 11 is free from the guiding walls 12.

In order to facilitate lateral displacement of the locking member, the outer cup portion 2 has, on its inside and in association with the aperture 9, two depressions 23, one at each short end of the aperture. On lateral displacement of the locking member 6, its one projection 18 will be accommodated in the one depression 23.

According to the present invention, the locking member 6 is manufactured from a resilient material and has, at the free end of the outer shank 11, an inwardly directed bulge 20 which, under the action of the spring forces inherent in the locking member 6, may be snapped into a recess 21 on the outside of the outer cup portion 2 (see FIG. 1). In such a snapped-in position, the bulge 20 prevents unintentional displacement of the locking member 6 in the opening direction.

The inherent resilient force in the locking member 6 also strives to keep the outer shank 11 in the guide 12. This spring force must be overcome before the locking member can be laterally displaced and dismounted.

In order to make for opening of the locking member, the outer cup portion 2 has, in association with its recess 21, a hollow 22 which permits access to the end surface of the outer shank 11 so that this, with the aid of a tool or a human nail, can be lifted out a sufficient distance in order that the bulge 20 will be free from the recess 21 and thereafter the whole of the locking member will be able to be displaced in the opening direction.

What is claimed is:

1. An ear cup comprising:
   an inner cup portion for forming a noise damping space and
   an outer cup portion for forming a space for accommodating electronics,
   electric connections and/or a current source mounted on the inner cup portion, the outer cup portion being fixable on the inner, and
   a locking device which includes a locking member disposed in a guide in the outer cup portion,
   wherein the locking member being movable between a locked position where the outer cup portion is fixed on the inner and an open position where the outer cup portion is removable from the inner;
   wherein the locking member and the outer cup portion have mutually cooperating retainer means which retain the locking member on the outer cup portion.

2. The ear cup as claimed in claim 1, wherein the outer cup portion covers a whole of an outside of the inner cup portion.

3. The ear cup as claimed in claim 1, wherein the guide is disposed to guide the locking member in a displacement movement.

4. The ear cup as claimed in claim 1, wherein the guide is disposed on an outside of the outer cup portion.

5. The ear cup as claimed in claim 1, wherein the locking member has a locking portion on an inside of the outer cup portion, the locking portion, in the locked position, being located in a locking recess on the inner cup portion.

6. The ear cup as claimed in claim 1, wherein the locking device further includes catch means engaging with one another in the locked position, one on an outside of the inner cup portion and one on an inside of the outer cup portion, the catch means being releasable from one another in the open position.

7. The ear cup as claimed in claim 1, wherein the locking member is produced from a resilient material, has and includes a bulge which, under action of inherent resilient forces, may be snapped into a recess in the outer cup portion in order to prevent unintentional displacement of the locking member to the open position.

8. The ear cup as claimed in claim 1, wherein the retainer means for fixedly retain the locking member on the outer cup portion when in the open position.

9. An ear cup comprising:
   an inner cup portion for forming a noise damping space and
   an outer cup portion for forming a space for accommodating electronics,
   electric connections and/or a current source mounted on the inner cup portion, the outer cup portion being fixable on the inner, and
   a locking device which includes a locking member disposed in a guide in the outer cup portion,
   wherein the locking member being movable between a locked position where the outer cup portion is fixed on the inner and an open position where the outer cup portion is removable from the inner;
   wherein the locking member has an inner shank interiorly in the outer cup portion, and an outer shank on an outside thereof, the locking member extending through an aperture in the outer cup portion, the retainer means including at least one projection which extends laterally out from the inner shank so that a width thereof over the projection is larger than a width of the aperture.

10. The ear cup as claimed in claim 9, wherein the inner shank has a recess in an edge located in register with the projection, the recess being of a depth which is larger than a projecting extent of the projection, whereby the locking member is mountable in and dismountable from the aperture by lateral displacement of the locking member so that the edge of the aperture is located in the recess.

11. The ear cup as claimed in claim 10, wherein the locking member has two opposing projections and two recesses disposed in association therewith.

* * * * *

UNITED STATES PATENT AND TRADEMARK OFFICE
CERTIFICATE OF CORRECTION

PATENT NO. : 8,189,801 B2
APPLICATION NO. : 11/912434
DATED : May 29, 2012
INVENTOR(S) : Henrik Heringslack It is certified that error appears in the above-identified patent and that said Letters Patent is hereby corrected as shown below:

Column 1
Line 38, delete "and" and insert -- an --, therefor.

Column 5
Line 5, in Claim 8, after "means" delete "for".

Signed and Sealed this
Twelfth Day of March, 2013

Teresa Stanek Rea
*Acting Director of the United States Patent and Trademark Office*